United States Patent [19]
Siegmund et al.

[11] Patent Number: 4,878,755
[45] Date of Patent: Nov. 7, 1989

[54] PROCESS AND DEVICE FOR MEASURING THE OPTICAL PROPERTIES OF THIN LAYERS

[75] Inventors: Hans-Joachim Siegmund, Babenhausen; Horst Schwiecker, Berlin, both of

[73] Assignee: Leybold Aktiengesellschaft, Hanau, Fed. Rep. of Germany

[21] Appl. No.: 881,708

[22] Filed: Jul. 3, 1986

[30] Foreign Application Priority Data

Mar. 29, 1986 [DE] Fed. Rep. of Germany ....... 3610733

[51] Int. Cl.$^4$ ............................................. G01B 11/06
[52] U.S. Cl. ..................................... 356/382; 356/357; 427/10
[58] Field of Search ............... 356/381, 382, 355, 357, 356/434; 427/10

[56] References Cited

U.S. PATENT DOCUMENTS 3,737,237  6/1973  Zuvasky ............................. 356/382
4,566,798  1/1986  Haas ..................................... 356/243

FOREIGN PATENT DOCUMENTS 65276  6/1978  Japan ...................................... 427/10

Primary Examiner—Richard A. Rosenberger
Attorney, Agent, or Firm—Felfe & Lynch

[57] ABSTRACT

Process for measuring the optical properties of thin layers while they are being built up in vacuum coating installations. For this purpose, at least one test object is passed through a stationary measuring light beam and the transmission behavior of the test object is evaluated by measurement. A reference point for the measurements is fixed in each case by reference measurements at intervals of time. In addition, at least one opaque measurement zone and at least one measuring zone, which does not attenuate the measuring light beam, are disposed in path of motion of the test object. The ratio of the measured value of the test object, decreased by the measured value of the opaque measuring zone, to the measured value of the nonattenuating measuring zone, decreased by the measured value of the opaque measuring zone, is formed by an arithmetic logic unit.

1 Claim, 2 Drawing Sheets

PROCESS AND DEVICE FOR MEASURING THE OPTICAL PROPERTIES OF THIN LAYERS

The invention relates to a process for measuring the optical properties of thin layers while they are being built up in vacuum coating installations. For this process, at least one test object is passed through a stationary measuring light beam, the transmission behavior of the test object being evaluated by measurement and, in each case, a reference point for the measurements is fixed by means of reference measurement at intervals of time.

Form the German Offenlegungsschrift No. 2,627,753 the use of a stationary measuring light beam, which emanates from a single source of measuring light, and from which a reference light beam may be split off, is known. The test object (a test glass) is stationary during the measurement and is disposed in the center of a substrate holder, the portion of the measuring light, passing through, being detected by a photodetector. A second photodetector is assigned to the reference light beam that has been split off and the ratio is formed from the output signals of the two photometers after appropriate amplification. While it has been possible to compensate largely, by these means, for brightness fluctuations of the measuring light source, varying changes in the two paths of rays, as well as the effects of different characteristic curves or of different operating points on the characteristic curves of the two photodetectors remain. This has negative effects on the accuracy of the test results.

It is furthermore known that, after repeated deflections and reflections at mirror systems, the reference light beam, which has been split off, can be routed to the same photodetector as the actual measuring light beam. This takes place alternately because of a chipping process, so that, by appropriately interrogating at the output of the photodetector by means of an evaluating circuit, the thereby formed, separate pulse sequences can be evaluated with respect to the desired compensation effect. The mirror systems, however, increase the cost of construction considerably and they are also subject to changes in the reflection values with time, so that the compensation effect aimed for is constantly accompanied by such errors.

From the German Offenlegungsschrift No. 3,135,444, it is known that a reference light beam may be omitted and that the whole of the spectrum of the measuring range can be portrayed in the form of absolute values by an expensive electronic circuit with intermediate storage of measured values and amplification factors. The measurements, however, are carried out once again on a test glass, which is stationary at least during the measurement and the position of which, with respect to the stream of coating material emanating from a source, is not identical with the position of the substrate to be coated, so that the build-up of the layers on the substrates does not necessarily agree with that on the test glass. Here also, a calibration must be carried out from time to time. This is accomplished, on the one hand, by measuring an unattenuated measuring light beam, that is, a measuring light beam that does not pass through any solid material and, on the other hand, by interrupting the measuring light beam completely by pushing an opaque object (0 screen) into the path of rays. In the first mentioned case, 100% of the intensity of the measuring light beam and, in the last mentioned case, 0% of the intensity falls on the photodetector. However, such a calibration cannot readily be carried out while the layer is being built up.

It is therefore an object of the invention to provide a process of the kind described at the beginning, which makes do with a simple, stationary path of rays and in which the movable test object is passed consecutively through the steam of coating material and through the measuring light beam and for which all possible influences on the result of the measurement are compensated for automatically after each measurement.

This objective is accomplished inventively for the process given initially owing to the fact that, in addition, at least one opaque measuring zone and one measuring zone, which does not attenuate the measuring light beam, are disposed in path of motion of the test object and that the ratio of the measured value of the test object, decreased by the measured value of the opaque measuring zone, to the measure value of the nonattenuating measurement zone, decreased by the measured value of the opaque measuring zone, is formed in an arithmetic logic unit and that the ratio is evaluated as the transmission value of the coated test object.

In this connection, the "opaque measuring zone" may be formed by any solid object, which temporarily and for a finite time blocks the path of rays completely. If the test object is disposed in a plate-shaped or spherical, metal substrate holder with several openings for accommodating individual substrates, the bridges between the openings can form the "opaque measuring zone".

The "measuring zone that does not attenuate" the measuring light beam can most easily be formed by an opening in the substrate holder, in which neither a test object nor a substrate is disposed.

In this way, two measured values, which always represent 0% and 100% of the intensity of the measuring light beam, are formed at the end of the single path of rays. The third value, namely the value measured for the test object itself, lies—at least in the case of a transparent test object—between the two limiting values. The computing operation, carried out in the arithmetic logic unit, corresponds to the relationship:

$$T = \frac{I_M - I_0}{I_{100} - I_0} \times 100 \ (\%)$$

in which $I_M$ = the portion of the measuring light beam, which has been transmitted by the test object and detected by the photo detector $I_O$ = the intensity of the radiation detected by the photodector when the measuring light beam is blocked completely $I_{100}$ = the radiation detected by the photodetector when the measuring light beam is completely unblocked.

The value of $I_0$ generally is very small and may even be zero. Scattered light effects or luminous radiation, which are produced while certain coating sources are being operated, can possibly be detected here. In any case, $I_M$, the measured value, varies proportionally with $I_{100}$, the maximum value of the intensity. Any fluctuation in the intensity of the source of the measuring light affects the numerator and denominator of the ratio mentioned, so that this influence can be compensated for mathematically in the shortest possible time. There are no other deviations, since there are neither separate paths of rays nor separate circuits with a different drift behavior. The mathematical compensation is also accomplished in the shortest possible time. If a substrate holder is used, which is in the form of a circular disk or sphere rotating about its axis and at the edge of which recesses for the substrate, a recess for the test object, as well as the inventive measuring zones are disposed, then the substrates, the test object and the aforementioned measuring zones pass several times consecutively through the stream of coating material, so that the layer as a whole is built up of numerous individual layers. After each individual passage through the stream of coating material, however, a measured value is obtained, for which all the effects of errors, insofar as such errors are still possible at all, are compensated for automatically.

It is understood that any condensation of coating material in the opaque measuring zone has no effect on the associated test signal and that the nonattenuating measuring zone, formed by an opening in the substrate holder, cannot bring about any condensation because the passage of material is not impeded, so that here also the test signal cannot be affected by the coating process.

The invention is not limited to the use of rotating substrate holders, but can also be used with linearly displaceable holders, which are moved consecutively past different coating sources or are moved in oscillating fashion relative to one or several coating sources.

One of the substrates or a special test glass can be used as test object; however, all substrates can also function consecutively as test objects. The latter case will, however, remain the exception. Substrates and/or test objects are passed alternately through the stream of coating material (or the streams of coating materials, if it is a question of coating with several materials) and through the measuring light beam, so that changes in the density of the stream of material, emanating from coating source, can be detected within an extremely short time and also controlled if the inventive measuring process for obtaining the actual value is used for a control process, which influences, for example, the output control of the source of the coating material.

The invention also relates to a device for implementing the initially given process with a vacuum chamber, in which a substrate holder is movably disposed and has facilities for holding at least one test object and for moving the test object along a path of motion, with a coating source, a measuring light source and a measuring light detector, which is connected with the measuring light source by means of a path of rays, the path of motion of the test object passing consecutively through the stream of material emanating from the coating source and through the path of rays.

As coating sources for this device, heatable vaporizers, atomizing cathodes, gas supplying devices in conjunction with energy sources for polymerizing monomers on the substrates, etc., can be used.

To accomplish the same objective, it is proposed inventively for the device given above that, aside from the test object, at least one opaque measuring zone and at least one measuring zone, which does not attenuate the measuring light beam, are disposed in the substrate holder, the substrate holder has signal transmitters for reporting the positions of the test object and of the measuring zones, and the outputs of the photodectector and the signal receiver are locked on to an arithmetic logic unit, in which the ratio of the measured value of the test object, decreased by the measured value of the opaque measuring zone, to the measured value of the nonattenuating measuring zone, decreased by the measured value of the opaque measuring zone, is formed and in which the ratio can be evaluated as the transmission value of the coated test object.

An example of the operation of the object of the invention is described in greater detail in the following by means of FIGS. 1 to 3.

Figure 1:
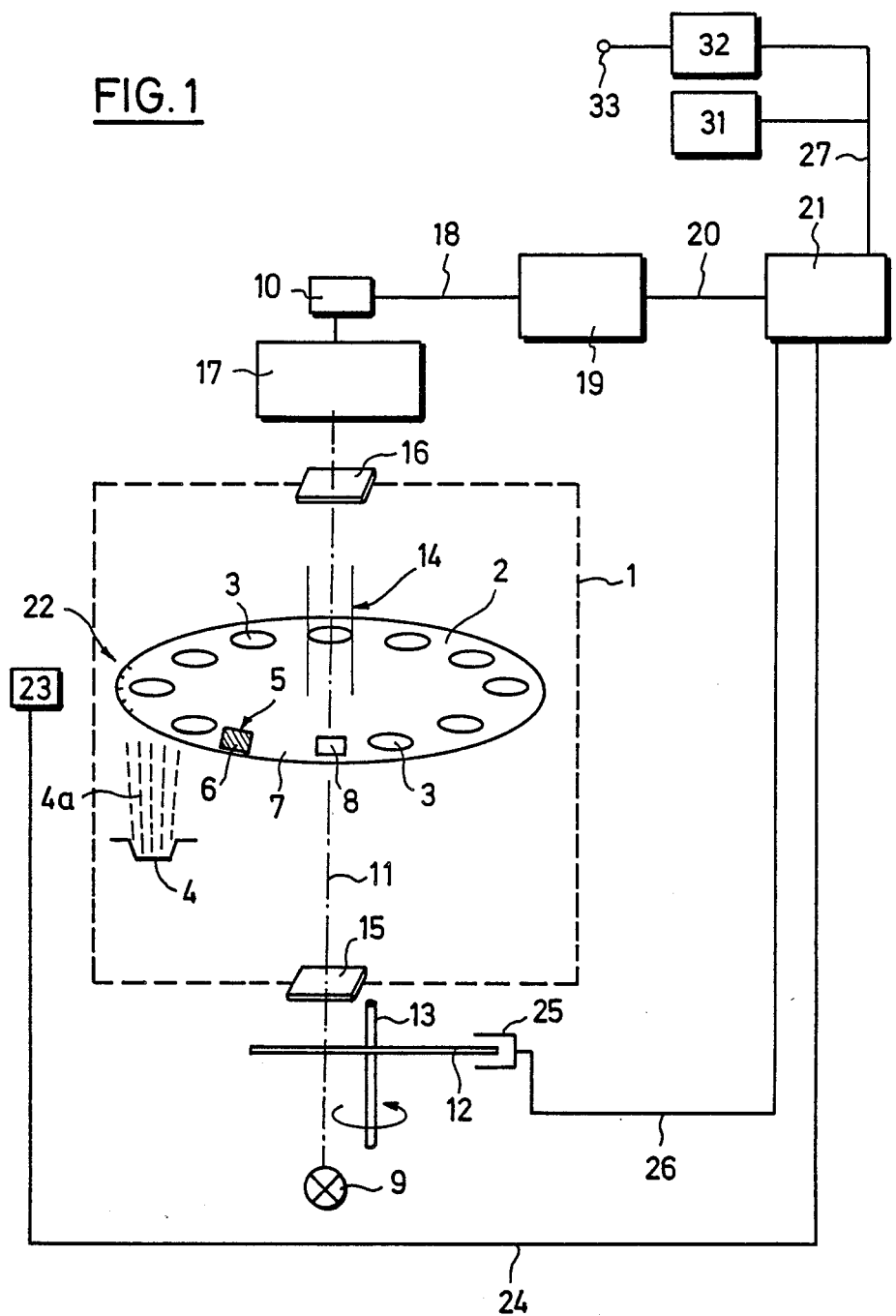
FIG. 1 shows a schematic representation of the device in conjunction with a block circuit diagram for processing signals.

In FIG. 1, the outline of a vacuum chamber 1 is shown by the broken line, in which the operating vacuum, required for the coating process, is maintained by means of vacuum pumps, which are not shown. A substrate holder 2, which is rortatable about a vertical axis and has the shape of a circular disk and in the edge region of which a number of recesses 3 is disposed for accommodating substrates, is disposed in the vacuum chamber 1. These substrates all have the same (circular) path of motion, which runs over the center of a source 4 for the coating material, disposed below the substrate holder 2. A further recess 5 for the test object 6, an opaque measuring zone 7 and a measuring zone 8, which does not attenuate the measuring light beam, also lie in the same path of motion as the recesses 3. As already explained above, the test object 6 advisably comprises a test glass, formed by glass disk with parallel faces, the measuring zone 7 comprises a solid part of the surface (bridge) of the substrate holder 2 and the measuring zone 8 comprises an open opening or a further recess in the substrate holder 2.

The optical measuring device, the so-called photometer, contains a source 9 of measuring light and a photodetector 10, between which an essentially linear, perpendicular path of rays 11 extends, which the measuring light beam, emanating from the source 9 of measuring light, follows, the path of rays 11 is also disposed in the path of motion of the substrate, the test object and the measuring zones and consequently is disposed excentrically to the axis of rotation of the substrate holder.

To compensate for environmental effects, the measuring light beam is divided into individual light pulses by a chopper disk 12, which rotates about an axis 13. The measuring light beam 14, only a part of the length of which is shown, passes through a first window 15 into the vacuum chamber 1 and leaves this chamber once again through a second window 16. From the spectrum of the measuring light beam, a particular frequency or a narrow frequency range is selected in a monochromator 17. By adjusting the monochromator 17, which may be constructed as filters, diffraction gratings or prisms, the optical properties can be investigated or measured over the whole of the spectrum of the source of measuring light. Care must be taken to ensure that the source 4 is disposed at such a distance laterally from the measuring light beam 14, that the coating material does not hit the window 16.

The output signals of the photodetector 10 are supplied over a line 18 to the interface 19, in which analog-digital conversion takes place. The output signal of the interface 19 is supplied over a line 20 to a central unit 21, which contains a digital, lock-in amplifier and an arithmetic logic unit, in which the inventive evaluation of the test signals takes place.

In order to achieve the necessary synchronization or triggering, the substrate holder has a series of signal transmitters 22, shown only schematically here, for reporting the position of the test object 6 and of the measuring zones 7 and 8 in combination with a signal receiver 23. The output of said receiver is also supplied over a line 24 to the central unit 21, in which the output signals of the photodetector 10 are assigned on the basis of time to the test object 6 or to the measuring zones 7 and 8. The signal transmitters 22 may, for example, a reed relay, responds as they move past. The edge region of the chopper disk 12 is also supplied with signal transmitters, which are not described in greater detail and which act on an additional signal receiver 25, which is connected over line 26 with the central unit 21.

Figure 2:
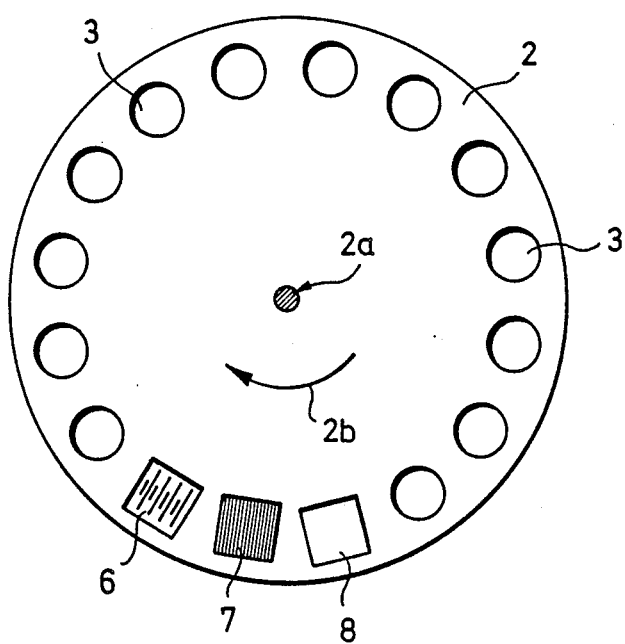
FIG. 2 shows a plan view of a rotatable substrate holder.
Figure 3:
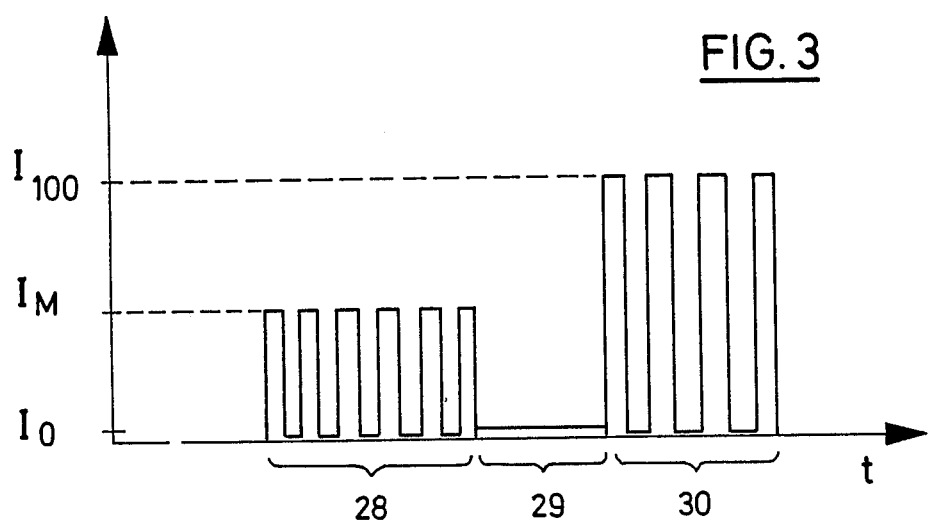
FIG. 3 shows a diagram of a sequence of signals, formed at the output of the photodetector as the test object, the opaque measuring zone and the unattenuated measuring zone pass through the measuring light beam.

The mode of action of the photometer arrangement is explained in greater detail by means of FIGS. 2 and 3. When the substrate holder 2 revolves about its axis 2a, the recesses 3 with the substrates, the test object 6, the opaque measuring zone 7 and the nonattenuating measuring zone 8 consecutively arrive at the path of rays 11 of the photometer. The path of motion of these elements is defined by a circle, which passes through the midpoint of said elements. Aside from the test signals, which are generated by the substrates and which are not intercepted by the triggering described further above, a first sequence of rectangular pulses, the height of which corresponds to the intensity $I_m$ of the portion of the measuring light beam transmitted by the test object 6, is formed as the substrate holder 2 rotates in the direction of the arrow 2b. The opaque measuring zone 7, subsequently passes through the measuring light beam, produces a test signal 29 with an extremely low lever $I_O$ at the output of the photodetector 10. This test signal 29 does not consist of a sequence of pulses, since the action of the chopper disk 12 is eliminated by the complete blockage of the measuring light beam. The test signal 29 is followed by a second sequence of rectangular pulses 30, the height of which corresponds to the unattenuated intensity $I_{100}$ of the measuring light beam. The frequency of the pulses corresponds to the rotational speed of the chopper disk 12, multiplied by the number of openings disposed in the chopper disk 12. The desired measured value is formed from the sequence of pulses, as well as from the test signal 29. This measured value is supplied over a line 27 to an indicator 31 or a controller 32, the controller having an output 33, over which the output of the source 4 can be controlled in a known manner. It is also possible to interrupt or switch off the coating process over in response to the output 33, for example, by swivelling a screen into the stream 4a of coating material, which emanates from the source 4.

We claim:

1. Apparatus for measuring the light transmission behavior of thin layers while they are being formed in a vacuum chamber with a coating source, in which a substrate holder is movably disposed and has facilities for holding at least one test object and for moving the test object along a path of motion, said apparatus comprising a measuring light source and a measuring light receiver, which is connected with the measuring light source by means of a path of rays, the path of motion of the test object passing consecutively through the stream of material emanating from the coating source and through the path of rays, wherein aside from the test object, at least one opaque measuring zone and at least one measuring zone, which does not attenuate the measuring light beam, are disposed in the substrate holder, the substrate holder has signal transmitters for reporting the positions of the test object and of the measuring zones and outputs of the photodetector and the signal receiver are locked on to an arithmetic logic unit, in which the ratio of the measured value of the test object, decreased by measured value of the opaque measuring zone, to the measured value of the nonattenuating measuring zone, decreased by the measured value of the opaque measuring zone, is formed and in which the ratio can be evaluated as the transmission value of the test object.

* * * * *